United States Patent [19]
Agarwala et al.

[11] Patent Number: 5,310,470
[45] Date of Patent: May 10, 1994

[54] CORROSIVITY SENSOR

[75] Inventors: Vinod S. Agarwala, Warminster; Fred Pearlstein, Philadelphia, both of Pa.

[73] Assignee: The United States of america as represented by the Secretary of the Navy, Washington, D.C.

[21] Appl. No.: 942,914

[22] Filed: Sep. 10, 1992

[51] Int. Cl.$^5$ .............................................. G01N 27/26
[52] U.S. Cl. .............................. 204/404; 204/153.11; 324/700
[58] Field of Search .......................... 204/153.11, 404; 324/71.2, 425, 448, 700

[56] References Cited

U.S. PATENT DOCUMENTS 4,780,664 10/1988 Ansuini et al. ........................ 324/700
4,994,159 2/1991 Agarwala et al. ................ 204/153.1

Primary Examiner—Aaron Weisstuch
Attorney, Agent, or Firm—James V. Tura; James B. Bechtel; Susan E. Verona

[57] ABSTRACT

A lightweight corrosivity sensor is provided which is thin enough to be embedded between the layers of a composite structure or placed on a surface beneath a coating. It comprises a thin non-conductive base and two electrically isolated conductive elements fixed to the surface thereof. Each conductive element comprises a bus bar and a plurality of strips extending from the bus bar and interdigitated with the strips of the other conductive element. The corrosivity sensor is connectable to a current measuring means for measuring the current across the two conductive elements as an indicator of the presence of a corrosive environment. A masking method of manufacturing such a sensor is also provided.

12 Claims, 2 Drawing Sheets

CORROSIVITY SENSOR

STATEMENT OF GOVERNMENT INTEREST

The invention described herein may be manufactured and used by and for the Government of the United States of America for governmental purposes without the payment of any royalties thereon or therefor.

BACKGROUND OF THE INVENTION

This invention relates generally to a corrosivity sensor and a method for its manufacture, and more particularly to a corrosivity sensor which is light enough for aircraft applications and thin enough for use in laminated composites and under coatings, and which is manufactured using masking techniques.

The destructive effects of corrosion are well known and efforts to minimize those effects are ongoing. The non-nuclear naval aircraft-carrier environment is a particularly corrosive one, with sulfur from aircraft-carrier stack gases combining with sea spray to provide a hostile environment which undermines the structural integrity of naval aircraft. Sensors for early detection of the presence of corrosive elements beneath coatings and between the layers of laminated composites would prompt early aircraft maintenance and repair and prevent disaster as well as save time and money.

Galvanic cell-type corrosion probes are currently used to determine the corrosivity of a surrounding medium. One such probe is disclosed in U.S. Pat. No. 4,994,159 to Agarwala et al. This kind of probe has been used on naval aircraft carriers to monitor the corrosivity of the sea environment due to moisture and salt. In operation, a thin film of water from the environment in question, usually in the form of sea spray, contacts the surface of the probe, acting as an electrolyte to complete the galvanic cell formed by two dissimilar metals exposed at the surface. In other words, this film of water acts as a pathway for current flow between the surfaces of the dissimilar metals. The probe is made by embedding within a matrix of insulating material a plurality of plates of alternately anodic and cathodic material, and then exposing the edges of the plates to form the surface. The probe's large size and heavy weight limit its usefulness in applications where space and weight are critical issues, such as on aircraft, and, in particular, within the composite layers of aircraft or on aircraft surfaces to be painted. The large size of this probe also limits its sensitivity because it will only detect the presence of electrolytic films which are large enough in area to bridge the gap between the exposed metals. Additionally, since this probe is made by exposing the edges of flat plates of anodic and cathodic material, the surface pattern thus formed is limited to straight-line strips. The probe is therefore not sensitive to the presence of a film spreading along the insulating surface between strips and parallel thereto.

Masking techniques have been used to manufacture printed circuit boards, but have not been applied to the formation of corrosivity sensors.

SUMMARY OF THE INVENTION

It is therefore an object of the present invention to provide a lightweight corrosivity sensor suitable for use on an aircraft. It is another object to provide a corrosivity sensor which is thin enough to be embedded between the layers of a composite structure or placed on a surface beneath a coating. It is still another object to provide a highly sensitive sensor which can quantitatively measure corrosivity. It is yet another object to provide early detection of a corrosive environment. It is also an object to provide an inexpensive method of manufacturing a thin, lightweight corrosivity sensor.

Briefly, these and other objects of the invention are accomplished by a corrosivity sensor comprising a thin non-conductive base and two electrically isolated conductive elements fixed to the surface thereof. Each conductive element comprises a bus bar and a plurality of strips extending from the bus bar. The strips of the two conductive elements are interdigitated. The corrosivity sensor is connectable to a means for measuring the current across the two conductive elements as an indicator of the presence of a corrosive environment. Masking techniques are used in the manufacture of the sensors.

These and other objects, advantages, and novel features of the invention will become apparent from the following detailed description of the invention when considered in conjunction with the accompanying drawings wherein:

DESCRIPTION OF THE PREFERRED EMBODIMENT

The present invention provides a sensor for detecting and measuring corrosivity, which sensor is thin enough to be used in situ either between the layers of a laminated composite or on the surface of a structure, either exposed to the environment or beneath a coating. The sensor is connectable to a means for measuring current as an indicator of the presence of corrosive elements in the immediate environment. Masking methods of manufacturing such a sensor are also provided.

Figure 1A:
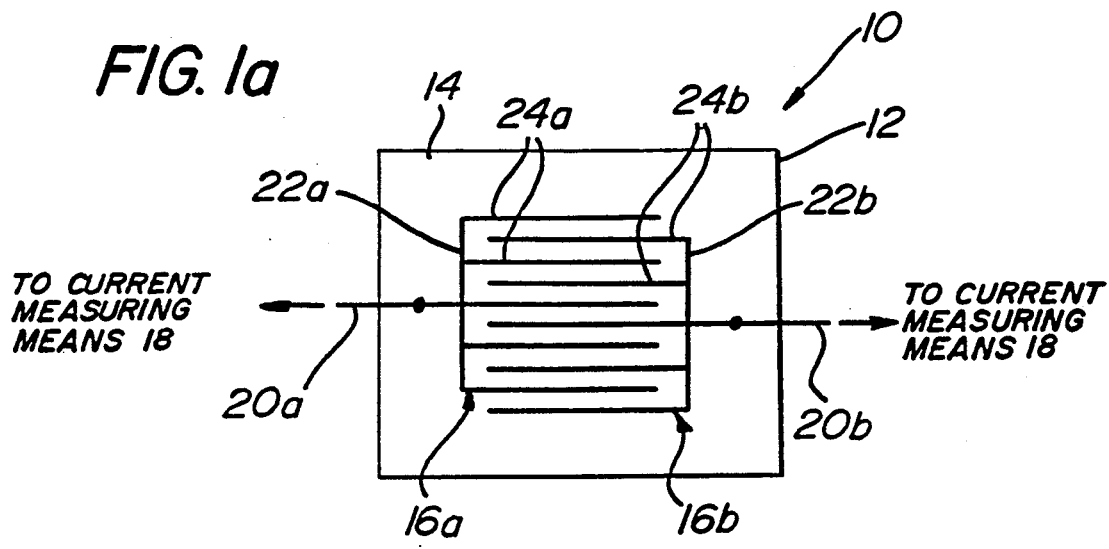
FIGS. 1a, 1b, and 1c are schematic diagrams of different embodiments of the corrosivity sensor of the present invention.
Figure 1B:
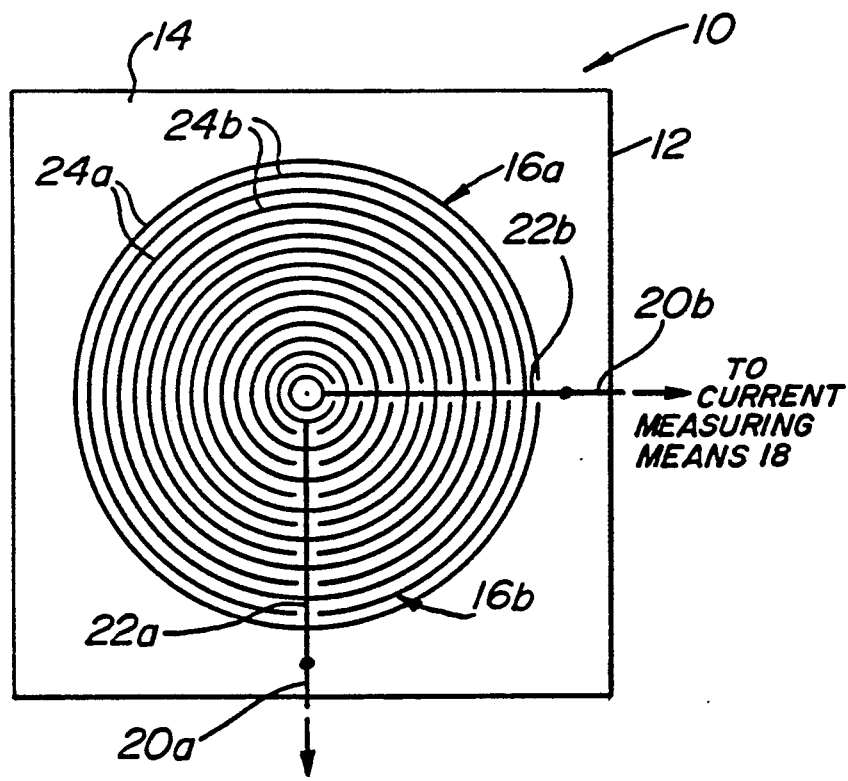
Figure 1C:
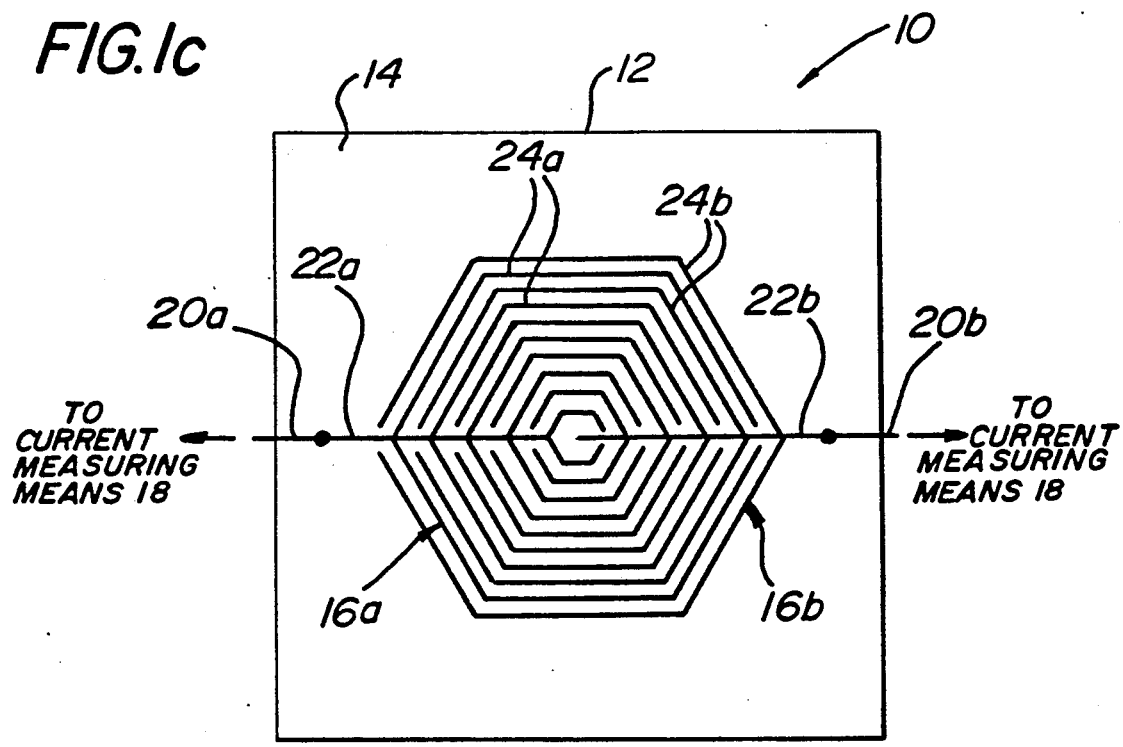

Referring now to the drawings wherein like characters designate like or corresponding parts throughout the several views, one sees in FIGS. 1a, 1b, and 1c diagrammatic views of three embodiments of a corrosivity sensor 10 of the present invention. A thin non-conductive base 12 of insulating material has fixed to its surface 14 two very thin conductive elements 16a and 16b electrically isolated from one another. Sensor 10 is connected to a current-measuring means 18 via wires 20a and 20b connected to elements 16a and 16b, respectively. The presence of moisture which contains corrosive elements is detected by monitoring current between conductive elements 16a and 16b when a film of the moisture contacts both elements on surface 14.

Non-conductive base 12 may be fabricated of any non-conducting material which is dimensionally stable and non-porous and which will not dissolve under processing conditions. Base 12 should be as thin as possible, its thinness being limited only by what thickness can withstand processing conditions and remain dimensionally stable. For example, base 12 may be a thin film or sheet of Kapton (Dupont), a polyimide which is available in sheets as thin as 0.3 mil thick, or glass-epoxy composite sheets, which are available as thin as 2 mils thick. In one embodiment of corrosivity sensor 10 of the present invention base 12 is an adhesive which can be fixed to any flat or gently curved substrate of interest. Conductive elements 16a and 16b are fixed to the adhesive layer. Such a sensor 10 may be applied like a decal to the substrate.

Each conductive element 16 is a very thin continuous layer of conductive material and comprises a bus bar 22 which commonly connects a series or plurality of strips 24 which extend therefrom. Strips 24 are preferably essentially parallel. Bus bars 22a and 22b also connect to wires 20a and 20b, respectively. Strips 24a and 24b of elements 16a and 16b are interdigitated so that the strips alternate between those of one conductive element and those of the other. Strips 24a and 24b can form any interdigitated pattern on surface 14, such as essentially parallel straight lines, as shown in FIG. 1a. A preferred pattern has essentially parallel strips 24 that form a rotationally symmetric geometric pattern, such as the concentric circles of FIG. 1b or the hexagonals of FIG. 1c. Of course, as shown in FIGS. 1b and 1c, strips 24 do not form closed circles or hexagonals, since elements 16a and 16b must be electrically isolated from each other. These rotationally symmetric configurations are preferred because they allow the moisture film to spread in any direction and still bridge the gap between elements 16a and 16b. This omnidirectionality makes sensor 10 insensitive to tilt, an important feature if it is to be used on aircraft. Strips 24a and 24b are preferably all of the same width and essentially equally spaced one from the next. The sensitivity of sensor 10 increases with the number of strips 24 per unit area and with decreasing distance therebetween. As an example, strips 24a and 24b may be less than 30 mils wide and less than 15 mils apart. Ten mil wide strips 24 spaced 3.5 mils apart have been found to be effective in detecting even very minor amounts of moisture and corrosive elements.

The optimum thickness of elements 16 balances the need for sensor 10 to be very thin so that it can be used under coatings or between the layers of a composite material, and the need for sensor 10 to be durable and have a useful lifespan. Processing conditions also limit how thin elements 16 can be. Elements as thin as 0.6 mil are achievable.

Surface 14 of base 12 should be hydrophilic, particularly when the distance between strips 24 is greater than 5 mils, so that moisture films will tend to be continuous as opposed to being isolated microdroplets. A hydrophilic surface 14 may be achieved by carefully cleaning the surface or by treating the surface with surfactants.

Conductive elements 16a and 16b may be of dissimilar materials, one acting as an anode and the other acting as a cathode, so that the presence of an electrolyte will generate galvanic current, the magnitude of which will be indicative of the corrosivity of the electrolyte or environment. The selection of materials may be governed by their relative electrochemical potentials or by what specific corrosive elements are being detected. The metals may also be selected to closely reflect the objects being corroded. One useful embodiment employs gold and zinc as the cathode and anode, respectively, a combination which is very sensitive to the presence of small amounts of moisture. Even moisture generated from breathing on such a gold-zinc sensor is detectable. Of various combinations studied, the gold-zinc combination for conductive elements 16a and 16b was found most reproducible and responsive to humidity changes during long-term exposure; it provided a relatively high current output (a few microamperes) even in less than 80% relative humidity. Other useful metal combinations include gold-iron, copper-zinc, gold-copper, tin-iron, nickel-chromium, and gold-cadmium.

Figure 2:
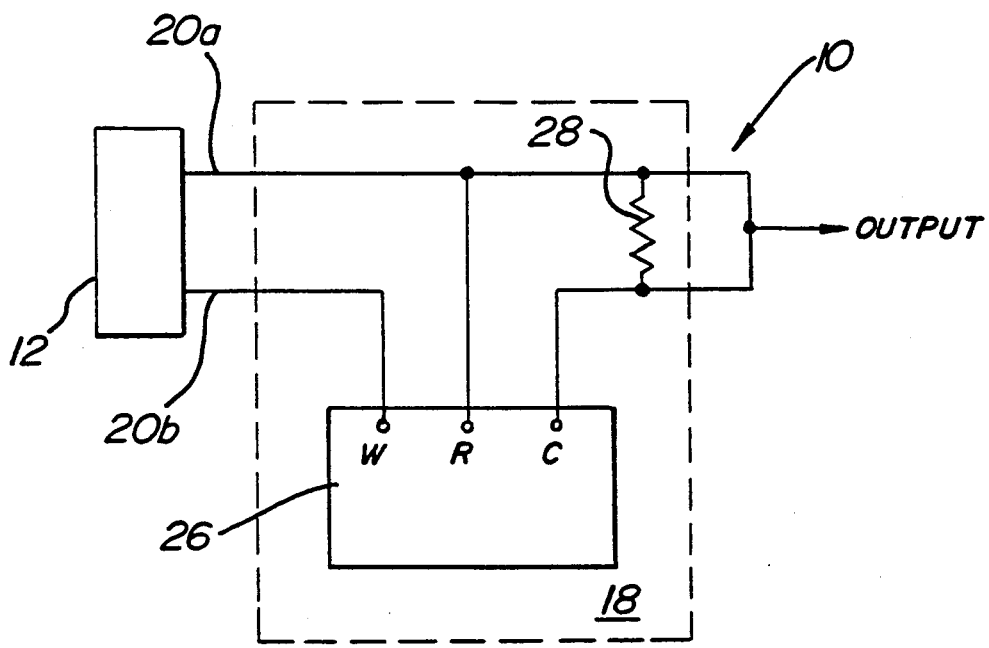
FIG. 2 is a diagrammatic view of the corrosivity sensor of the present invention showing the current measuring means.

To measure the corrosion current generated between elements 16a and 16b when of dissimilar metals, wires 20a and 20b connect bus bars 22a and 22b to current measuring means 18. Current measuring means 18 may be any means for measuring relatively small amounts of current, the smaller the current that can be measured the more sensitive the device to the first signs of corrosion. For example, as shown in FIG. 2, current measuring means 18 may be a zero resistance ammeter comprising a potentiostat 26 in which the potential between the working (w) and the counter (c) terminals thereof is adjusted to zero. A standard resistance box 28 is connected between the reference (r) and the counter (c) terminals to convert the current into a potential drop for amplification and recording. Current variations of up to three orders of magnitude can be recorded easily with such an arrangement without significantly changing the resistance between the reference (r) and the counter (c) terminals. A 100-kohm resistor is adequate to measure current in the range of 0.01 to 10 mA. Using sensitive measuring means allows current to be measured, indicating the onset of corrosion, long before any visible signs of corrosion would be present.

Means may be operatively connected to the output of current measuring means 20 to measure the quantity of electricity produced (coulombs), and the amount of anodic material corroding can be calculated by Faraday's law using the known value of anodic surface area. Means may also be incorporated for calculating the corrosion rate in mass per surface area of anodic material corroding and for calculating the corrosion rate over time. All such calculating means are known to those skilled in the art.

In another application of sensor 10 of the present invention both conductive elements 16 are made of the same material. In this case the presence of an electrolytic film is measured by applying a voltage across elements 16a and 16b and then measuring the current therebetween in order to ascertain the resistance therebetween, which is a function of the corrosivity or conductivity of the electrolytic film. The more corrosive the moisture is, the lower the measured resistance will be.

The present invention provides the following method of manufacturing the sensor according to the invention. A layer of non-conductive material, such as 1-mil thick Kapton or 10-mil thick glass-epoxy sheet, is provided as base 12. A layer of copper, such as copper foil 0.35 to 1.4 mils thick, is applied, such as by adhesively bonding with heat and pressure, to base 12. Alternatively, a thin non-conductive film may be coated directly with a layer of electroless copper 0.05 to 0.1 mil thick by autocatalytic chemical reduction deposition. Masking techniques are used to apply resist to selected areas of the copper layer. For example, photoresist may be applied to the copper layer and photographic imaging used so that the photoresist remains over only two areas of the copper layer where elements 16 will be. The exposed, unwanted, copper is then dissolved away chemically, after which the remaining photoresist is removed, leaving two electrically isolated thin copper elements corresponding to conductive elements 16. Electrical contact is then made with one of the copper elements, and the selected metal, such as gold, is electrodeposited thereupon. A nickel electrodeposit may be interposed between the copper and the gold to serve as a diffusion barrier. In the preferred embodiment, 0.05- to 0.1-mil thick nickel and 0.03- to 0.08-mil thick gold are applied. Electrical contact is then made with the other copper element, which is electrodeposited with the other selected metal, such as zinc, to a thickness of preferably between 0.5 and 1.5 mils. Preferably, the more anodic of the two dissimilar metals is deposited to a greater thickness than the other. The zinc element may first be electrodeposited with nickel and gold, if desired.

In an alternative process, the photoresist can be photographically developed so that copper is exposed only where elements 16 are to be fixed. The exposed areas are then electrodeposited with first nickel and then gold. The photoresist is removed and the newly-exposed copper is dissolved away, leaving two gold conductive elements 16 on non-conductive surface 14. One of conductive elements 16 may then be contacted electrically and electrodeposited with zinc.

The above-described photographic imaging method can be used to produce a sensor 10 with very close and narrow strips 24, and is therefore the preferred method. However, other masking techniques, such as silk screening with stripping resist, may be used to provide a pattern of copper in the desired location on base 12.

A corrosivity sensor 10 having an adhesive as base 12 can be made in the following manner on a stainless steel foil or any other metal foil upon which electrodeposits do not adhere firmly. Using masking techniques, the metal foil is covered with resist except for an area to become conductive element 16a. The exposed metal foil is then electrodeposited with gold, 0.08 to 0.1 mil in thickness, to form conductive element 16a. Conductive element 16a is then covered with resist, and, using masking techniques, the metal foil is exposed at the area to become conductive element 16b. This area is electrodeposited with zinc, 0.1 to 0.2 mil in thickness, to form conductive element 16b. The resist is then removed chemically to leave only conductive elements 16 on the metal foil. The electrodeposited side of the foil is applied to an adhesive film or layer upon the substrate of interest. Conductive elements 16 will adhere more firmly to the adhesive layer than to the metal foil, so the foil is then peeled off, leaving conductive elements 16 bonded to the adhesive, which forms base 12. Wires 20a and 20b can be applied to conductive elements 16 using conductive epoxy cement or similar material.

When a sensor 10 according to the invention using gold and zinc as conductive elements 16a and 16b was coated with polyurethane aircraft paint and exposed to 100 percent relative humidity, initial current flow was less than one nanoampere, which increased to over 10 nanoamperes after about 130 hours of exposure. When another such sensor was coated with a 5-mil polyurethane paint film and exposed to five percent NaCl salt spray, the currents recorded were in the nanoamperes range up to approximately 500 hours, and thereafter the current steadily increased until it reached a near plateau value of over 5000 nanoamperes after 750 hours of exposure. This threshhold is an indicator of paint failure and initiation of substrate corrosion.

Some of the many advantages and novel features of the invention should now be readily apparent. A lightweight and highly sensitive corrosivity sensor is provided which is thin enough to be embedded between the layers of a composite component or placed on a surface beneath its coating without affecting the mechanical and functional properties of the component or coating. Furthermore, an inexpensive method of manufacturing such a thin, light-weight corrosivity sensor has been provided.

Other embodiments and modifications of the present invention may readily come to those of ordinary skill in the art having the benefit of the teachings presented in the foregoing description and drawings. Therefore, it is to be understood that the present invention is not to be limited to such teachings presented, and that such further embodiments and modifications are intended to be included within the scope of the appended claims.

What is claimed is:

1. A corrosivity sensor, comprising:
    a non-conductive base 10 mils or less thick and having a surface;
    a first conductive element composed of a first material fixed to the surface, said first conductive element further comprising a bus bar and a plurality of strips extending therefrom; and
    a second conductive element composed of a second material different from the first material fixed to the surface and electrically isolated from said first conductive element, said second conductive element further comprising a bus bar and a plurality of strips extending therefrom, and being interdigitated with the strips of said first conductive element, the strips of said first and second conductive elements being less than 30 mils wide and less than 15 mils apart, whereby galvanic current may be generated between adjacent strips in the presence of an electrolyte.

2. The corrosivity sensor of claim 1, further comprising a current measuring means operatively connected to measure the current across said first and second conductive elements.

3. The corrosivity sensor of claim 1, wherein said first conductive element is a thin layer of gold.

4. The corrosivity sensor of claim 3, wherein said second conductive element is a thin layer of zinc.

5. The corrosivity sensor of claim 1, wherein said base is glass-epoxy sheet.

6. The corrosivity sensor of claim 1, wherein said base is polyimide sheet.

7. The corrosivity sensor of claim 1, wherein said base is an adhesive.

8. The corrosivity sensor of claim 1, wherein the strips of said first and second conductive elements ar essentially parallel.

9. The corrosivity sensor of claim 8, wherein the strips of said first and second conductive elements are straight lines.

10. The corrosivity sensor of claim 8, wherein the strips of said first and second conductive elements form a rotationally symmetric geometric pattern.

11. The corrosivity sensor of claim 10, wherein the strips of said first and second conductive elements form circles.

12. The corrosivity sensor of claim 10, wherein the strips of said first and second conductive elements form hexagonals.

* * * * *